US012667720B2

(12) United States Patent
Arnar et al.

(10) Patent No.: US 12,667,720 B2
(45) Date of Patent: Jun. 30, 2026

(54) BIOSTIMULATOR DELIVERY SYSTEM HAVING TETHER CABLE

(71) Applicant: Pacesetter, Inc., Sylmar, CA (US)

(72) Inventors: Bernhard Arnar, Minnetrista, MN (US); Keith Victorine, Santa Clarita, CA (US); Shawn X. Chen, Santa Clarita, CA (US); Mike Sacha, Champlin, MN (US); Mark Krans, Hopkins, MN (US); Andy Servi, Plymouth, MN (US); Jeremiah Blue, Andover, MN (US); Adam Weber, Eden Prairie, MN (US)

(73) Assignee: Pacesetter, Inc., Sylmar, CA (US)

( * ) Notice: Subject to any disclaimer, the term of this patent is extended or adjusted under 35 U.S.C. 154(b) by 843 days.

(21) Appl. No.: 17/356,055

(22) Filed: Jun. 23, 2021

(65) Prior Publication Data

US 2022/0409885 A1 Dec. 29, 2022

(51) Int. Cl.
*A61N 1/05* (2006.01)
*A61M 25/00* (2006.01)
(Continued)

(52) U.S. Cl.
CPC ......... *A61N 1/057* (2013.01); *A61M 25/0068* (2013.01); *A61M 25/0082* (2013.01);
(Continued)

(58) Field of Classification Search
CPC ...... A61N 1/057; A61N 1/056; A61N 1/0563; A61N 1/37512; A61N 1/3756;
(Continued)

(56) References Cited

U.S. PATENT DOCUMENTS 4,742,360 A * 5/1988 Carolus ................. H01Q 1/103
343/903
5,314,461 A * 5/1994 Borghi ................. A61N 1/0573
607/127
(Continued)

FOREIGN PATENT DOCUMENTS

CN 105705116 A 6/2016
WO 2018204753 A1 11/2018

OTHER PUBLICATIONS

Extended European Search Report from related EP Application No. 22179815.0, mailed on Nov. 8, 2022, 6 pages.
(Continued)

*Primary Examiner* — Tan-Uyen T Ho
*Assistant Examiner* — Osama Nemer
(74) *Attorney, Agent, or Firm* — WOMBLE BOND DICKINSON (US) LLP

(57) ABSTRACT

A biostimulator delivery system having a tether cable, is described. A connector can be mounted on the tether cable to connect to a biostimulator. The connector can be a protuberance that lodges within the biostimulator, or a threaded connector that screws into the biostimulator. The tether cable has a stranded cable configuration, including several strands extending about a core strand in a helical direction. The stranded cable structure resists breaking under bending stresses typically seen during a tether mode used during delivery of the biostimulator. The tether cable reliably secures the biostimulator to the delivery system in the tether mode. Other embodiments are also described and claimed.

16 Claims, 10 Drawing Sheets

(51) Int. Cl.
    *A61M 25/01*       (2006.01)
    *A61N 1/375*      (2006.01)

(52) U.S. Cl.
    CPC ..... *A61M 25/0136* (2013.01); *A61N 1/37512*
    (2017.08); *A61N 1/3756* (2013.01); *A61N*
    *2001/058* (2013.01)

(58) Field of Classification Search
    CPC .......... A61N 2001/058; A61N 1/37205; A61N
    1/372; A61N 1/37518; A61M 25/0068;
    A61M 25/0082; A61M 25/0136
    See application file for complete search history.

(56) References Cited

U.S. PATENT DOCUMENTS

| | | | | |
|---|---|---|---|---|
| 7,174,220 | B1 * | 2/2007 | Chitre .................... | A61N 1/056 |
| | | | | 600/374 |
| 9,750,944 | B2 * | 9/2017 | Struve ................. | A61N 1/3718 |
| 2012/0035474 | A1 * | 2/2012 | Deckman ................. | A61B 8/12 |
| | | | | 600/439 |
| 2012/0095539 | A1 * | 4/2012 | Khairkhahan ..... | A61N 1/37205 |
| | | | | 607/116 |
| 2012/0197373 | A1 * | 8/2012 | Khairkhahan ......... | A61N 1/057 |
| | | | | 607/122 |
| 2012/0271386 | A1 * | 10/2012 | Li ........................... | C22F 1/183 |
| | | | | 607/116 |
| 2015/0119796 | A1 * | 4/2015 | Finch .................... | A61F 2/2493 |
| | | | | 604/57 |
| 2016/0067447 | A1 * | 3/2016 | Paspa ................. | A61N 1/37205 |
| | | | | 606/129 |
| 2016/0128819 | A1 | 5/2016 | Giordano et al. | |
| 2017/0086975 | A1 * | 3/2017 | Gilmore ............. | A61B 17/0401 |
| 2017/0119999 | A1 * | 5/2017 | Kelly ................... | A61N 1/0587 |
| 2017/0319847 | A1 * | 11/2017 | Ho ...................... | A61B 17/3468 |
| 2018/0104452 | A1 * | 4/2018 | Goodman .......... | A61B 17/3468 |
| 2018/0296824 | A1 * | 10/2018 | De Kock ............... | A61N 1/059 |
| 2018/0320756 | A1 * | 11/2018 | Campbell ............. | D07B 1/005 |
| 2019/0175219 | A1 | 6/2019 | Goodman et al. | |
| 2019/0290323 | A1 * | 9/2019 | Chun ................. | A61B 17/3468 |
| 2020/0101299 | A1 * | 4/2020 | Arnar .................. | A61B 17/3439 |
| 2020/0345396 | A1 * | 11/2020 | Rickheim .......... | A61B 17/3468 |
| 2020/0346000 | A1 * | 11/2020 | Kerns ............... | A61M 25/0067 |
| 2021/0138252 | A1 * | 5/2021 | Eby ..................... | A61N 1/37512 |
| 2023/0158315 | A1 * | 5/2023 | Mar ................... | A61N 1/37518 |
| | | | | 607/36 |

OTHER PUBLICATIONS

Office Action from related EP Application No. 22179815.0, mailed on Mar. 13, 2024, 3 pages.

Office Action from related EP Application No. 22179815.0, mailed on Jul. 30, 2024, 3 pages.

Office Action from related EP Application No. 22179815.0, mailed on Oct. 7, 2025, 4 pages.

First Office Action dated Dec. 23, 2025 from related Chinese Patent Application No. 202210718370.3, 12 pages including translation.

\* cited by examiner

BIOSTIMULATOR DELIVERY SYSTEM HAVING TETHER CABLE

BACKGROUND

Field

The present disclosure relates to biostimulators and related transport systems. More specifically, the present disclosure relates to transport systems for delivery of leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Leadless cardiac pacemakers incorporate electronic circuitry at the pacing site and eliminate leads, thereby avoiding shortcomings associated with conventional cardiac pacing systems. Leadless cardiac pacemakers can be anchored at the pacing site, e.g., in a right ventricle and, for dual-chamber pacing, in a right atrium, by an anchor. A delivery system can be used to deliver the leadless cardiac pacemakers to the target anatomy.

SUMMARY

Existing leadless biostimulator systems may have a tether assembly to attach a leadless biostimulator to a catheter-based delivery system. The tether assembly may employ tethers that are manufactured by grinding a profile into a continuous length of wire. The ground wire can include a protuberance, or "bullet," at a distal end, which can be position within the leadless biostimulator to releasably connect the biostimulator to the delivery system. Prior to releasing the biostimulator at the target anatomy, the delivery system can operate in a "tether mode," in which the leadless biostimulator is freely supported by the tether assembly without additional support from a catheter of the delivery system. The tether of the tether assembly can experience substantial bending stresses in the tether mode, which have the potential to cause fatigue failures of the tether material. Such failures, e.g., tether breakage, could lead to an undesirable loss of the leadless biostimulator within a patient anatomy. Accordingly, there is a need for a biostimulator delivery system having a tether assembly that resists breaking under the bending stresses experienced during the tether mode.

A biostimulator delivery system having a tether cable is described. In an embodiment, the delivery system includes an elongated catheter extending from a handle to a docking cap. The docking cap can be rotationally coupled to the elongated catheter. For example, a torque cable can extend from the handle to the docking cap, and torque can be transmitted through the torque cable to rotate the docking cap relative to the elongated catheter. The docking cap can include a docking cavity to receive an attachment feature of a biostimulator, and thus, rotation of the docking cap can also rotate the biostimulator. Accordingly, the delivery system can rotate the biostimulator to drive a fixation element of the biostimulator into a target tissue.

The biostimulator can be retained relative to the elongated catheter by a tether assembly. The tether assembly can extend from the handle, through the elongated catheter, into an attachment feature of the biostimulator. For example, the tether assembly can include a connector at a distal end of a tether cable, and the connector can be lodged within and/or screwed into the attachment feature to connect the biostimulator to the delivery system via the tether cable. The biostimulator may be so held, for example, in a tether mode in which the biostimulator is freely supported on the tether cable distal to, and without the support of, the docking cap. In the tether mode, the tether cable can experience substantial bending modes within a beating heart.

The tether cable can be configured to flex freely and to resist breaking under the bending modes experienced during use. In an embodiment, the tether cable includes a core strand surrounded by several side strands. For example, a first plurality of strands can extend about the core strand in a first helical direction. The cable can be multi-layered. For example, a second plurality of strands can extend about the core strand in a second helical direction, between the core strand and the first plurality of strands. The first helical direction and the second helical direction can be opposite to each other to contribute to efficient torqueability.

In an embodiment, the delivery system includes several tethers in the tether assembly. For example, a first tether and a second tether can extend in parallel to each other. The tethers can include respective connectors at distal ends of the tether cables to engage a channel of the attachment feature. More particularly, the connectors can be aligned to lodge within the channel. Accordingly, the dual-tether configuration can attach the delivery system to the biostimulator.

In an embodiment, the delivery system includes a single tether in the tether assembly. For example, a single tether cable can include a threaded connector at a distal end of the cable. The threaded connector can engage a mating thread in the channel of the attachment feature, and thus, can be screwed into the attachment feature. Accordingly, the single-tether configuration can attach the delivery system to the biostimulator.

The delivery system can include support tubes, e.g., hypotubes, that extend from the handle to a proximal end of the tether cable(s). The support tubes can efficiently transmit axial loads to the tether cables. The delivery system may also include a retaining coil that wraps about the tethers of the dual-tether tether assembly. The retaining coil can constrain the tether cables to reduce the likelihood that the cables will drift away from each other, causing the connectors to misalign and unintentionally disengage from the attachment feature.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings.

DETAILED DESCRIPTION

Embodiments describe a biostimulator transport system, such as a biostimulator delivery system, having a tether cable. As described below, the biostimulator transport system can be used to deliver a biostimulator into a heart of a patient to pace cardiac tissue. The biostimulator may, however, be used in other applications, such as deep brain stimulation. Thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a tether cable. Similarly, "proximal" may indicate a second direction opposite to the first direction. Such terms are provided to establish relative frames of reference, however, and are not intended to limit the use or orientation of a biostimulator delivery system to a specific configuration described in the various embodiments below.

In an aspect, the biostimulator delivery system includes a tether assembly for connecting the delivery system to a leadless biostimulator. The tether assembly includes a tether cable, which is both flexible and strong. More particularly, the tether cable has a stranded cable configuration including several side strands helically wrapped about a core strand. Each strand is small in diameter, and thus, bending stresses experienced by each strand are lower than a bending stress that would be experienced by a tether of a similar size formed from a single wire. Accordingly, bending stresses experienced by the tether cable for a given bend radius can be reduced such that the tether assembly can securely and reliably retain the biostimulator during delivery to a target anatomy.

Figure 1:
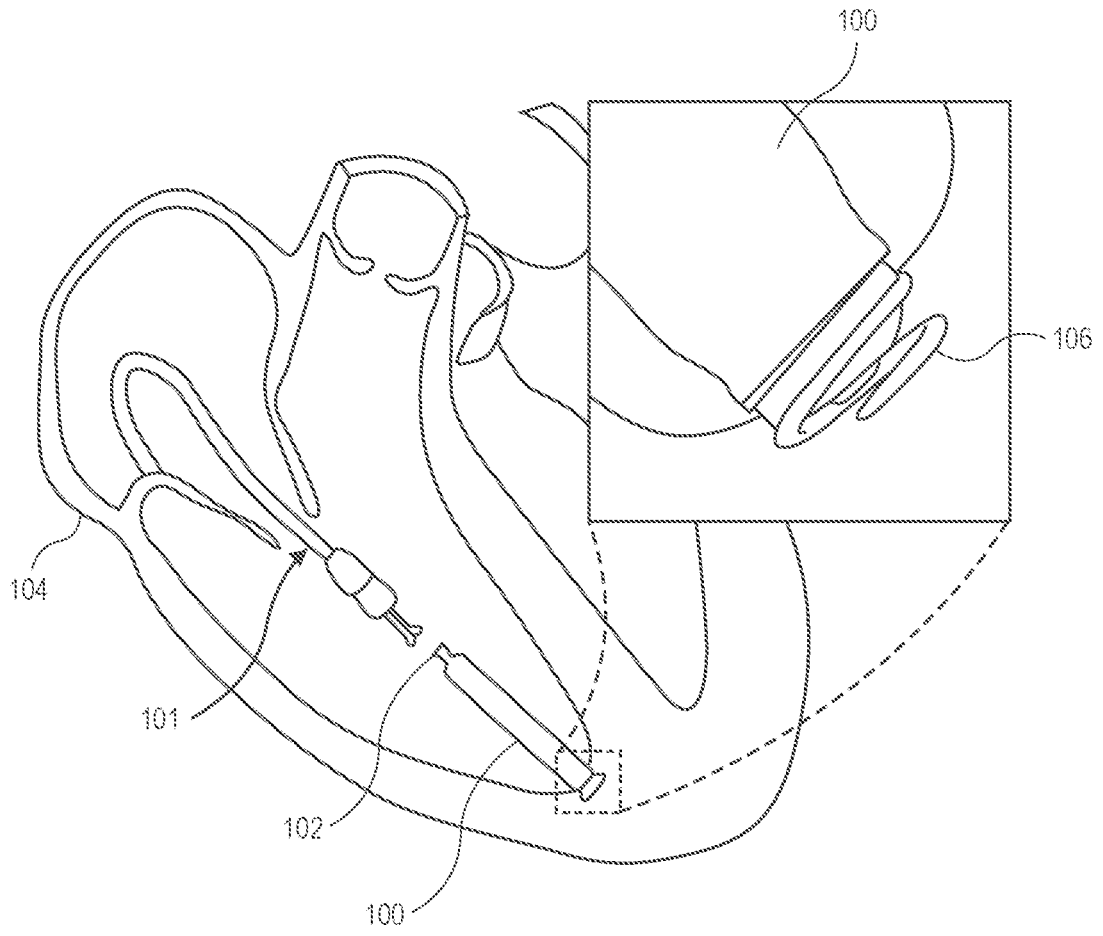
FIG. 1 is a diagrammatic cross section of a patient heart illustrating an example implantation of a biostimulator in a target anatomy, in accordance with an embodiment.

Referring to FIG. 1, a diagrammatic cross section of a patient heart illustrating an example implantation of a biostimulator in a target anatomy is shown in accordance with an embodiment. A cardiac pacing system includes one or more biostimulators 100 and a biostimulator transport system, e.g., a biostimulator delivery system 101. The biostimulator delivery system 101 can deliver the biostimulator(s) 100 to respective target anatomical sites in a patient heart 104. Alternatively, the biostimulator transport system can retrieve the biostimulator(s) 100 from the patient heart 104.

The biostimulator(s) 100 can be leadless, e.g., may be leadless cardiac pacemakers. Each biostimulator 100 can be placed in a cardiac chamber, such as a right atrium and/or right ventricle of the patient heart 104. Delivery (or retrieval) of the biostimulator 100 is facilitated by attaching the biostimulator 100 to a distal end of the biostimulator delivery system 101. More particularly, the biostimulator delivery system 101 can connect to an attachment feature 102 of the biostimulator 100.

The biostimulator 100 can be attached to an inside or outside of the cardiac chamber. Attachment of the biostimulator 100 to the target tissue can be accomplished via one or more fixation elements 106, such as helical anchors. Alternatively, the one or more fixation elements can include outward splaying splines that engage the target tissue to attach the biostimulator 100 to the target anatomy. In a particular embodiment, the leadless pacemaker can use two or more electrodes located on or within a housing of the leadless pacemaker for pacing the cardiac chamber upon receiving a triggering signal from internal circuitry and/or from at least one other device within the body.

Figure 2:
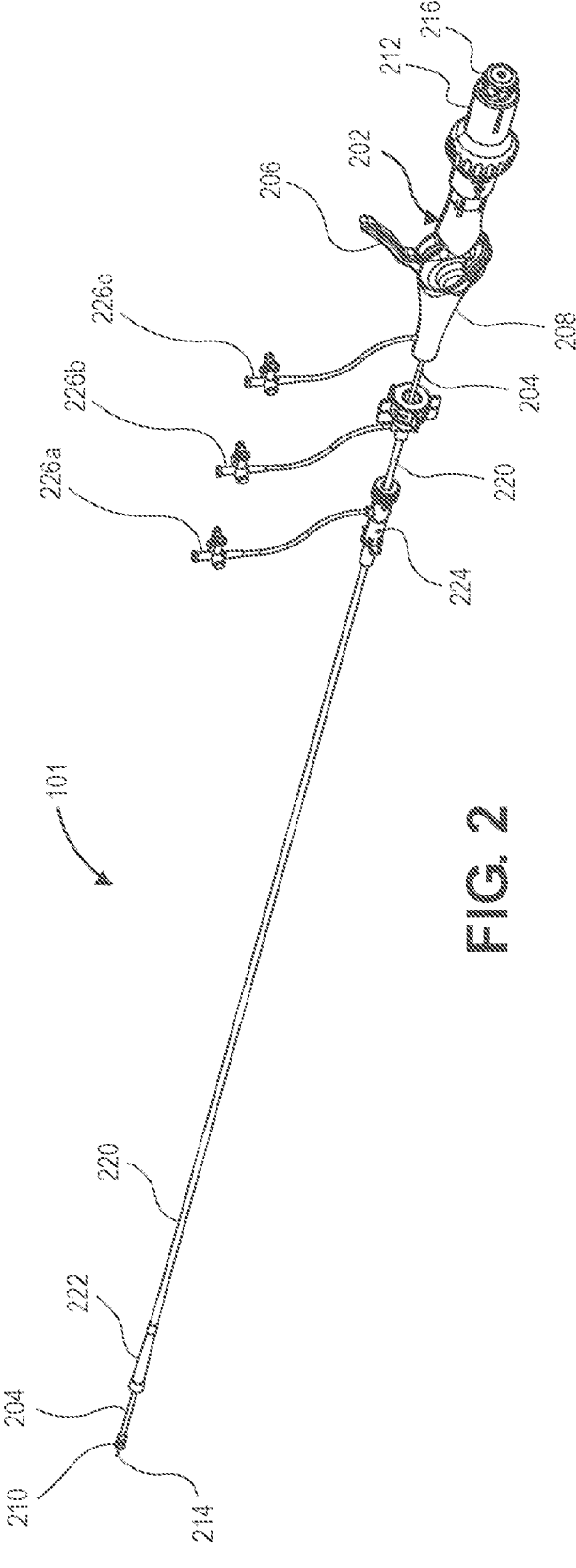
FIG. 2 is a perspective view of a biostimulator transport system, in accordance with an embodiment.

Referring to FIG. 2, a perspective view of a biostimulator transport system is shown in accordance with an embodiment. A biostimulator transport system may be used for delivery and/or retrieval of the biostimulator 100, e.g., a leadless pacemaker, into or from a patient. For example, the biostimulator transport system can be the biostimulator delivery system 101 used for delivery of the biostimulator 100 into the patient. Alternatively, the biostimulator transport system can be a biostimulator retrieval system. The transport system is primarily referred to as being the delivery system for brevity below, however, such reference is non-limiting.

The biostimulator delivery system 101 can include a handle 202, and an elongated catheter 204 extending distally from the handle 202 to a distal catheter end. The handle 202 can include several portions and features that allow a user to provide inputs at a proximal end of the system that translate to outputs at the distal end of the system. For example, the elongated catheter 204 can be a deflectable catheter, and an operator can use the handle 202 to steer the distal catheter end in the patient. In an embodiment, the handle 202 includes a deflection lever 206 that can be used to deflect the distal catheter end. By pivoting the deflection lever 206 toward a distal handle portion 208 of the handle 202, the operator can cause a pull ring assembly to apply off-axis compression to the elongated catheter 204, resulting in lateral deflection of the distal catheter end.

Figure 10:
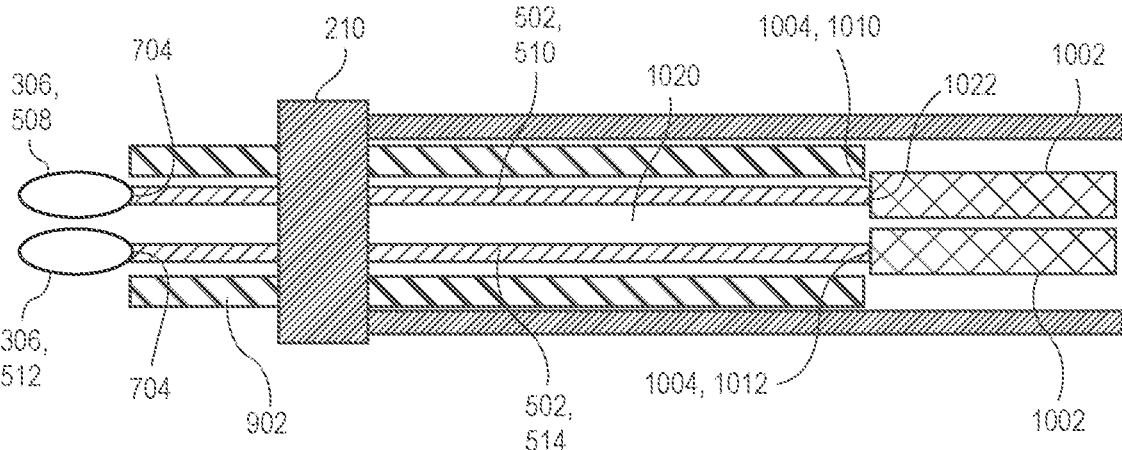
FIG. 10 is a cross-sectional view of a biostimulator delivery system, in accordance with an embodiment.

The handle 202 can be used to apply a torque to a docking cap 210 at the distal end of the system. The docking cap 210 can be rotationally coupled to the elongated catheter 204. In an embodiment, the handle 202 includes a first handle portion 212. The first handle portion 212 can be rotationally and/or longitudinally moveable relative to the distal handle portion 208. For example, the distal handle portion 208 can be coupled to the elongated catheter 204 and the first handle portion 212 can be coupled to a torque shaft (FIG. 10). An operator can rotate the first handle portion 212 relative to the distal handle portion 208 to cause the docking cap 210, which is rotationally linked to the first handle portion 212, to rotate relative to the elongated catheter 204, which is rotationally linked to the distal handle portion 208.

In an embodiment, the handle 202 can be used to cause longitudinal or rotational motion of a tether assembly 214 of the biostimulator delivery system 101. The handle 202 can include a second handle portion 216. Movement of the second handle portion 216 relative to another handle portion, e.g., the first handle portion 212, can cause relative motion between one or more tethers of the tether assembly 214 and/or another component of the biostimulator delivery system 101. For example, longitudinal movement of the second handle portion 216 relative to the first handle portion 212 can cause a first tether of the tether assembly 214 to move longitudinally relative to a second tether of the tether assembly 214. Alternatively, longitudinal movement of the first handle portion 214 and the second handle portion 216 relative to the distal handle portion 208 can cause the tethers to move relative to the docking cap 210.

In an embodiment, the biostimulator delivery system 101 includes a protective sheath 220 mounted on the elongated catheter 204. The protective sheath 220 can be slidably disposed on the elongated catheter 204. The protective sheath 220 can include an atraumatic end 222, e.g., a soft, funnel-shaped distal portion, that can slide distally over the distal catheter end of the elongated catheter 204 and/or the biostimulator 100 (not shown). The atraumatic end 222 can have an outer dimension, which may be larger than a proximal portion of the protective sheath 220. For example, the atraumatic end 222 may flare in a distal direction to a funnel opening that can advance over a docking cap 210 of the biostimulator delivery system 101. An outer dimension of the atraumatic end 222 can be larger than a region of the protective sheath 220 supporting a valve bypass tool 224.

The valve bypass tool 224 can be slidably disposed on the protective sheath 220 such that a distal portion of the valve bypass tool 224 can slide distally over the distal catheter end of the elongated catheter 204 and/or the atraumatic end 222 of the protective sheath 220. More particularly, the valve bypass tool 224 can be inserted into an access introducer to gain access to the patient vasculature, and after access is established, the distal portion of the protective sheath 220 and/or the distal end of the elongated catheter 204 can be advanced through the valve bypass tool 224 into the patient.

The valve bypass tool 224, the protective sheath 220, and the elongated catheter 204 can have respective flush ports 226a, 226b, and 226c extending respectively therefrom. Each of the longitudinal bodies are displaceable proximal-distal relative to each other, and thus, the flush ports can be used to introduce and/or flush saline or other fluids between the longitudinal bodies or through the respective components in different relative positions.

Figures 3, 4:
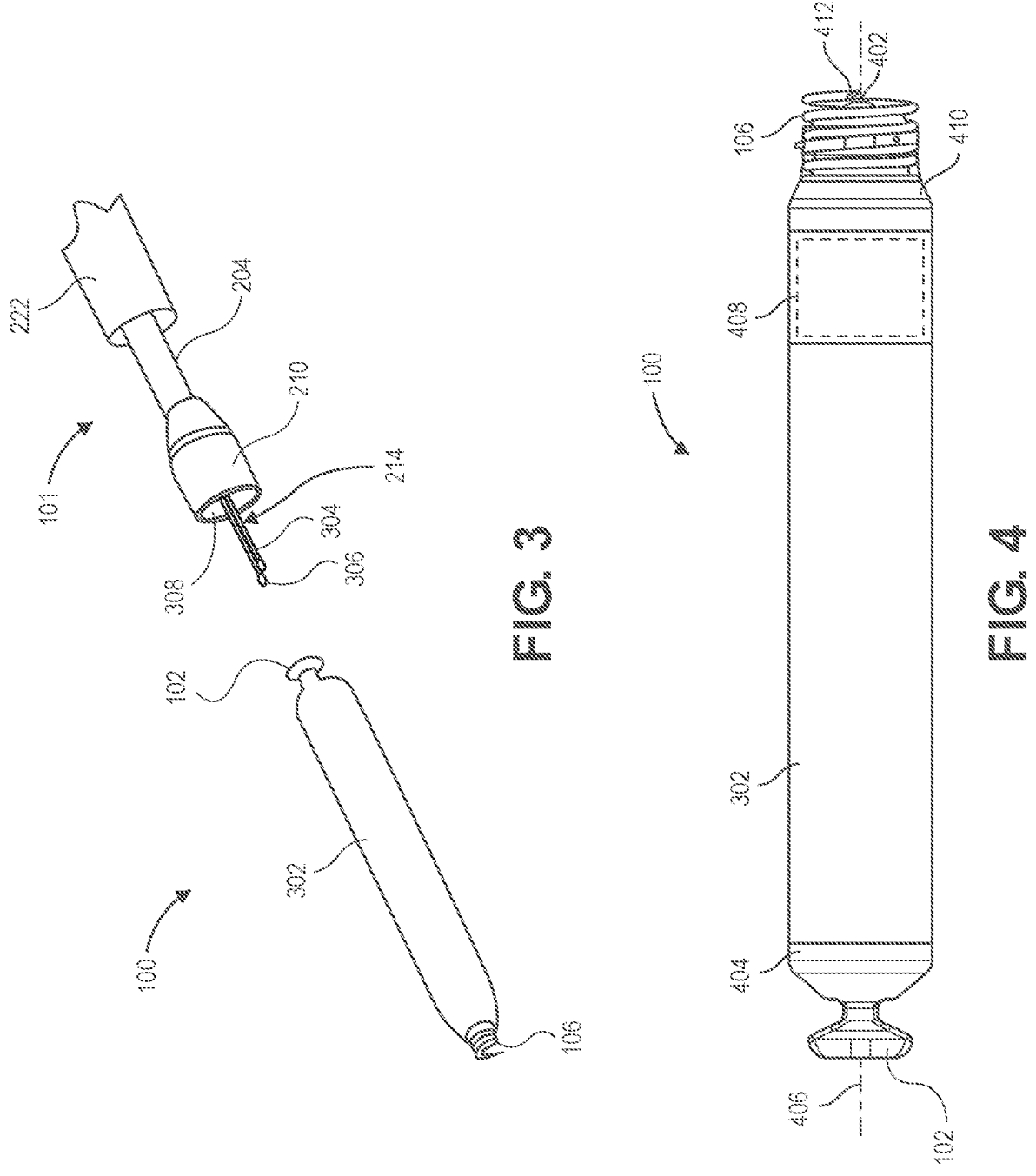
FIG. 3 is a distal perspective view of a biostimulator transport system having a docking cap to receive a biostimulator, in accordance with an embodiment.
FIG. 4 is a side view of a leadless biostimulator, in accordance with an embodiment.
Figure 5:
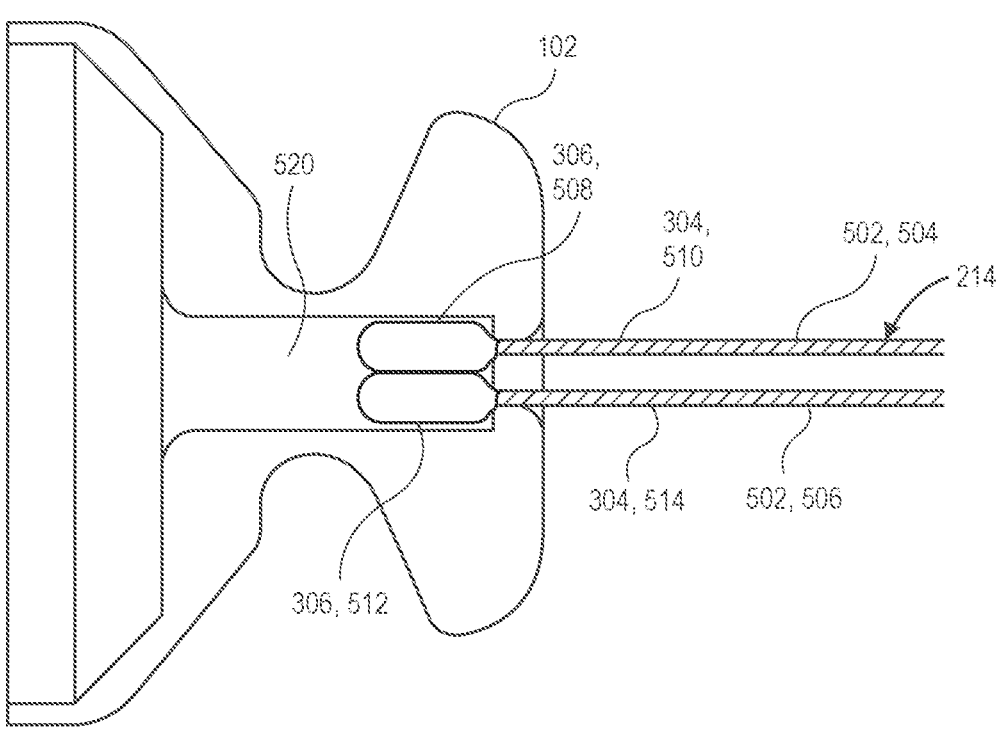
FIGS. 5-6 are cross-sectional views of a tether assembly engaging and releasing an attachment feature of a biostimulator, in accordance with an embodiment.
Figure 6:
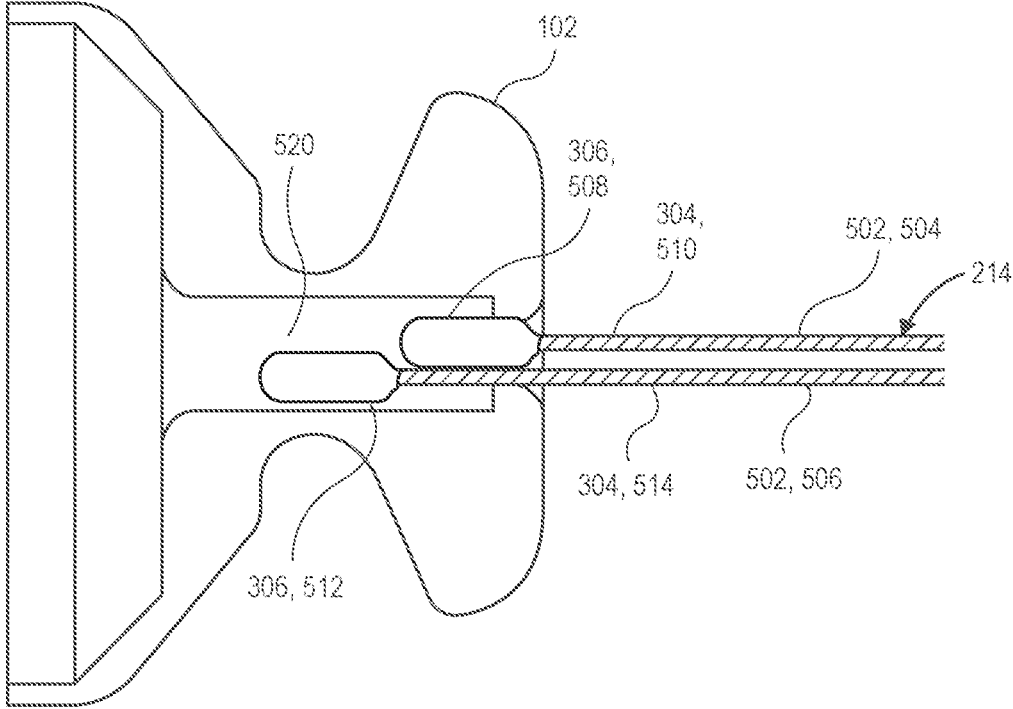
Figure 13:
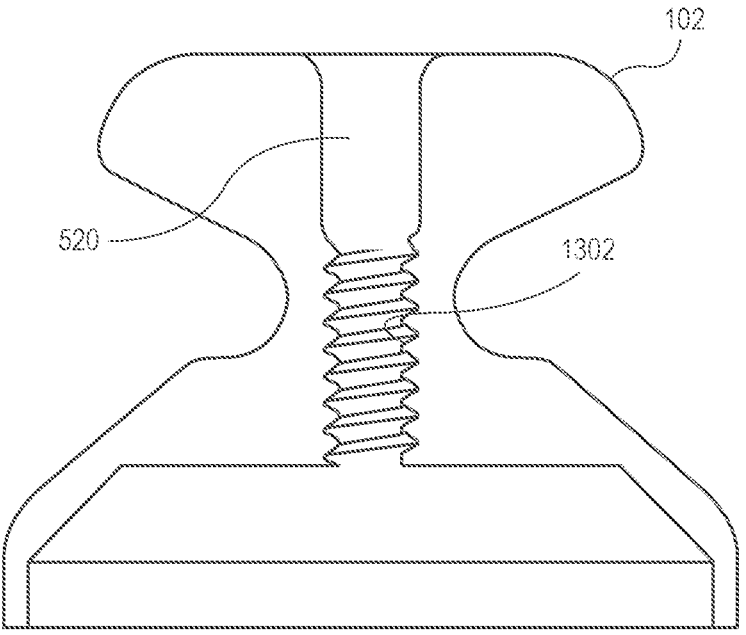
FIG. 13 is a cross-sectional view of an attachment feature of the biostimulator, in accordance with an embodiment.

Referring to FIG. 3, a distal perspective view of a biostimulator transport system having a docking cap to receive a biostimulator is shown in accordance with an embodiment. The distal catheter end of the elongated catheter 204 may be selectively connectable to the biostimulator 100. More particularly, the biostimulator delivery system 101 can include the tether assembly 214 extending from the handle 202 through the elongated catheter 204 to engage the biostimulator 100. The biostimulator 100 can therefore be mounted on the distal catheter end of the elongated catheter 204. In an embodiment, the biostimulator 100 includes the attachment feature 102. The attachment feature 102 can be, for example, a protuberance extending proximally from a housing 302 of the biostimulator 100. In an embodiment, the attachment feature 102 includes a channel shaped and sized to receive one or more tethers of the tether assembly 214 (FIGS. 5-6 and 13). More particularly, the tether assembly 214 can include a tether cable 304 and a connector 306 sized to fit within the channel. The connector 306 can be at a distal cable end of the tether cable 304, and may connect directly, e.g., by screwing into a mating connector of the attachment feature 102, or indirectly, e.g., by lodging within the channel of the attachment feature 102. Accordingly, the tether assembly 214 can connect the biostimulator 100 to the biostimulator delivery system 101.

In an embodiment, the docking cap 210 includes a docking cavity 308. The docking cavity 308 is sized and shaped to receive the attachment feature 102. More particularly, the attachment feature 102 can have a shape and size that fits within the docking cavity 308. When the tether(s) of the tether assembly 214 are locked within the attachment feature 102, the tether(s) can be retracted to pull the biostimulator 100 toward the docking cap 210. As the biostimulator 100 moves toward the docking cap 210, the attachment feature 102 can insert into the docking cavity 308. Accordingly, the docking cavity 308 can receive the attachment feature 102 to dock the biostimulator 100 to the biostimulator delivery system 101 for delivery or retrieval from the patient.

Referring to FIG. 4, a side view of a leadless biostimulator is shown in accordance with an embodiment. The biostimulator 100 can be a leadless cardiac pacemaker that can perform cardiac pacing and that has many of the advantages of conventional cardiac pacemakers while extending performance, functionality, and operating characteristics. The biostimulator 100 can have two or more electrodes, e.g., a distal electrode 402 and a proximal electrode 404, located within, on, or near the housing 302 of the biostimulator 100. In an embodiment, the fixation element 106 forms a portion of the distal electrode 402. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 302 has a longitudinal axis 406, and the distal electrode 402 can be a distal pacing electrode mounted on the housing 302 along the longitudinal axis 406. The housing 302 can contain a primary battery to provide power for pacing, sensing, and communication, which may include, for example, bidirectional communication. The housing 302 can optionally contain an electronics compartment 408 to hold circuitry adapted for different functionality. For example, the electronics compartment 408 can contain circuits for sensing cardiac activity from the electrodes, circuits for receiving information from at least one other device via the electrodes, circuits for generating pacing pulses for delivery via the electrodes, or other circuitry. The electronics compartment 408 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site by one or more actively engaging mechanisms or fixation mechanisms, such as a screw or helical member that screws into the myocardium (or optionally, tines). In an embodiment, the biostimulator 100 includes the fixation element 106 coupled to the housing 302. The fixation element 106 can be a helical element to screw into target tissue. More particularly, the fixation element 106 can extend helically from a flange 410 of the biostimulator 100, which is mounted on the housing 302, to a distal helix tip 412.

The distal helix tip 412 can be located distal to the distal electrode 402 (a centrally located electrode). Accordingly, when the biostimulator 100 contacts the target tissue, the distal helix tip 412 can pierce the tissue and the housing 302 can be rotated to screw the fixation element 106 into the target tissue to pull the distal electrode 402 into contact with the tissue. By contrast, the housing 302 can be rotated to unscrew the fixation element 106 from the target tissue to retrieve the biostimulator 100.

Referring to FIG. 5, a cross-sectional view of a tether assembly engaging an attachment feature of a biostimulator is shown in accordance with an embodiment. The tether assembly 214 can include several tethers 502. In an embodiment, the tether assembly 214 includes a first tether 504 and a second tether 506. Each tether of the tether assembly 214 can have a respective connector 306 and tether cable 304. For example, the first tether 504 can include a first connector 508 mounted on a first tether cable 510. Similarly, the second tether 506 can include a second connector 512 mounted on a second tether cable 514.

When the tether connectors 306 are placed within a channel of the attachment feature 102 and aligned in an axial direction, e.g., with a plane transverse to the longitudinal axes passing through both connectors 306, the connectors 306 are in an aligned state and the leadless pacemaker is engaged to the delivery system. When aligned, the overall dimension of the connectors 306 can be greater than the channel entrance, and thus, the connectors can engage the step in the channel 520 to connect the attachment feature 102 to the tether assembly 214.

The biostimulator 100 is shown in a tether mode in FIG. 5. After the biostimulator 100 is affixed to the target tissue, the tether assembly 214 can remain engaged with the attachment feature 102 while the docking cap 210 is retracted from the attachment feature 102, allowing the biostimulator 100 to be loosely coupled to the delivery system. The tether assembly 214 can remain engaged with the attachment feature 102 because a combined cross-sectional dimension of the connectors 306 may be greater than a dimension of the channel 520 entering the attachment feature 102. The tether assembly 214 may therefore become lodged within the channel 520 to connect the biostimulator 100 to the biostimulator delivery system 101.

In the tether mode, biostimulator 100 is held only by the two flexible tethers 502, and is not rigidly attached to the biostimulator delivery system 101. When the biostimulator delivery system 101 is in the tether mode, the tether assembly 214 can impart minimal force against the attachment feature 102, and thus, the motion of the biostimulator 100 in a free state (e.g., after the biostimulator 100 is released from the biostimulator delivery system 101) may be emulated. Accordingly, the integrity of the fixation of the biostimulator 100 to the target tissue can be assessed. Electrical performance of the biostimulator 100 may also be evaluated in the tether mode. For example, a threshold voltage (a minimum voltage required to transmit a pacing pulse to the heart tissue), impedance, and current of injury can be assessed in the tether mode, prior to releasing the biostimulator 100 from the biostimulator delivery system 101.

In the tether mode, movement of the biostimulator 100 may be quite dynamic and can impart substantial bending stresses to the tethers 502. Such bending stresses may lead to fatigue failures of the tether material. For example, in a case in which tethers 502 are formed from single wires (nickel titanium wires ground into a final shape having the protuberant connector 306 at a distal end of a tether body), bending stresses experienced by the tethers may exceed the tether strength, and the tethers can crack or break proximal to the attachment feature 102. On the other hand, tethers 502 formed from tether cables 304, as described below, can be quite flexible and resistant to fatigue failure.

Referring to FIG. 6, a cross-sectional view of a tether assembly releasing an attachment feature of a biostimulator is shown in accordance with an embodiment. The tethers 502 can be misaligned in the axial direction to release the biostimulator 100 at the target site. For example, the first handle portion 212 can be connected to the first tether 504 and the second handle portion 216 can be connected to the second tether 506, and relative motion between the handle portions can cause the respective connectors 306 of the tethers 502 to misalign. When misaligned, a combined transverse dimension of the connectors 306 may be less than a dimension of the channel 520 entering the attachment feature 102, and the tether assembly 214 may therefore be retracted and removed from the attachment feature 102. More particularly, the tether assembly 214 can be dislodged from the attachment feature 102 to release biostimulator 100 from the biostimulator delivery system 101.

Figure 7:
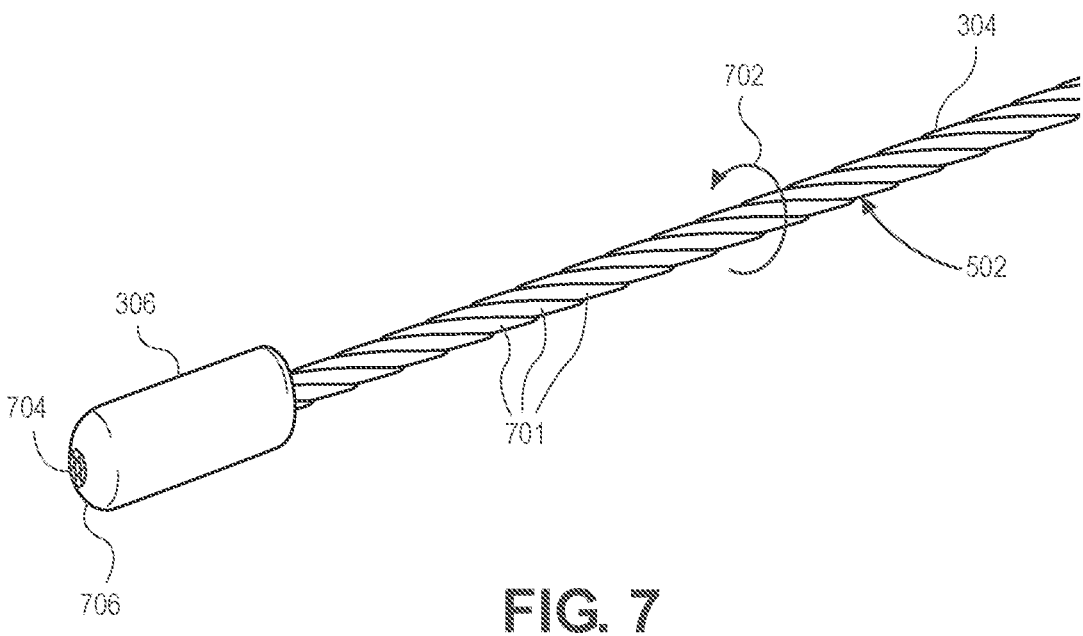
FIG. 7 is a perspective view of a tether assembly, in accordance with an embodiment.

Referring to FIG. 7, a perspective view of a tether assembly is shown in accordance with an embodiment. To reduce the bending stress experienced by the one or more tethers 502 of the tether assembly 214, a diameter of the tether body can be reduced. Bending stress is proportional to the diameter of the wire making up the tether body, and thus, for a given bend radius the stress may be reduced by reducing a cross-sectional dimension of the constituent parts of the tether body.

In an embodiment, each tether 502 of the tether assembly 214 includes a tether cable 304 having several strands 701 forming the tether body to minimize the cross-sectional dimension of the constituent parts of the tether body. The tether cable 304 can include several strands 701, and one or more of the strands can extend in a first helical direction 702 about a central axis of the tether cable 304. The strands 701 can wind around the central axis between a proximal cable end at the handle 202, and a distal cable end 704. The multi-stranded, twisted cable can provide the same tensile strength as a solid wire, yet may be more flexible and fatigue resistant.

The multi-stranded, twisted cable can be a cable formed from metal filars, as described below, or the cable may be a fibrous cable formed from strands or filars of other materials. For example, the twisted cable can be a fibrous thread or yarn that includes fibers wound around the central axis to form the tether structure. The fibers can be polymer or otherwise non-metallic fibers. In an embodiment, the fibers form a fibrous thread that provides the multi-stranded, twisted cable having the same tensile strength as a solid wire yet more flexibility and fatigue resistance. The fibrous thread can be a textile, e.g., having twisted, woven, or otherwise interlaced fibers to form the flexible and strong tether structure.

A connector 306 can be attached to the tether cable 304 at the distal cable end 704. For example the connector 306 can have an annular cross-sectional profile, e.g., a tubular shape, and the tether cable 304 can extend through a central hole in the annular connector 306. The connector 306 may then be attached to the tether cable 304, e.g., using a mechanical, thermal, or adhesive bond. For example, the connector 306 can be attached to the tether cable 304 by crimping, swaging, welding, etc. In an embodiment, a distal tip 706 of the connector 306 may have a lead-in to provide for smooth engagement into the channel 520 of the attachment feature 102. For example, the distal tip 706 can be dome-shaped, have a chamfer, or include another transition surface between the distal face of the connector 306 and a sidewall of the connector 306.

Figure 8:
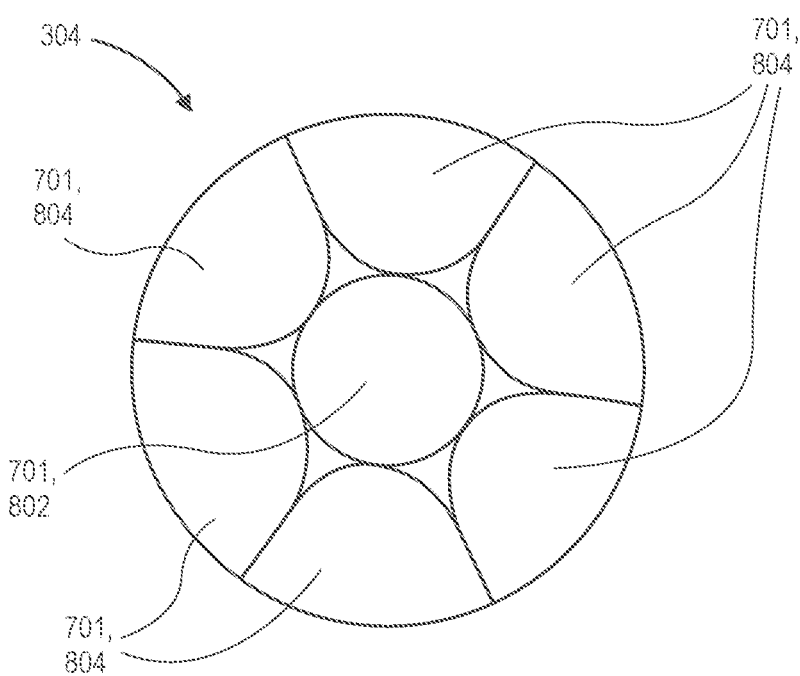
FIG. 8 is a cross-sectional view of a tether cable, in accordance with an embodiment.

Referring to FIG. 8, a cross-sectional view of a tether cable is shown in accordance with an embodiment. The tether cable 304 can be a constant-diameter, multi-filar cable. In an embodiment, the tether cable 304 includes a core strand 802, and several strands 701, e.g., a first plurality of strands 804, extending about the core strand 802. The core strand 802 can extend longitudinally along the central axis of the tether cable 304. By contrast, the strands 701 that wrap about the core strand 802 can be radially offset from the central axis, and can twist, e.g., in the first helical direction 702, around the core strand 802.

In an embodiment, each of the strands 701 is formed from the same material. For example, the core strand 802 and the filars wrapping about the core strand 802 can be formed from a cobalt-based metal alloy. The cobalt-based metal alloy may provide greater stiffness than a nickel-titanium alloy, although the latter may also be used to form the filars.

The strands 701 of the multi-filar tether cable 304 can have a same strand dimension. For example, each strand can have a filar diameter of 0.0022 inch. In the case of a one-by-six design, i.e., one central strand surrounded by six outer strands, the combined dimension of the tether cable 304 may be 0.0066 inch. In an embodiment, however, the outer wires may be swaged to produce a circular outer profile of the tether cable 304, and to bond the cable strands. In such case, the core strand 802 can have a round cross-sectional profile, and the first plurality of strands 804 can have a non-round cross-sectional profile. For example, the outer cable strands 804 can be deformed to have the flattened shape illustrated in FIG. 8. Accordingly, the combined dimension may be reduced from 0.0066 inch to 0.0063 inch, by way of example.

Figure 9:
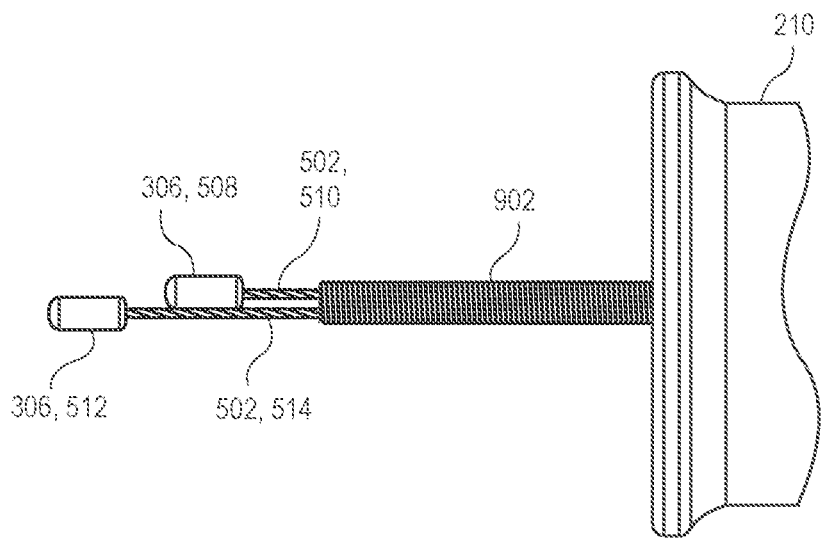
FIG. 9 is a side view of a tether assembly including a retaining coil, in accordance with an embodiment.

Referring to FIG. 9, a side view of a tether assembly including a retaining coil is shown in accordance with an embodiment. The multi-filar configuration of the tether cables can be flexible, and the tether bodies may tend to bow outward, away from each other, when the tether assembly 214 is placed in a curve or otherwise spent. It may be beneficial to have a stabilizing structure to ensure that the tethers 502 remain near each other, even under such conditions, because bowing of the tether bodies can cause the connectors 306 to undesirably misalign. Accordingly, in an embodiment, the biostimulator delivery system 101 includes a retaining coil 902 constraining the first tether cable 510 and the second tether cable 514. The retaining coil 902 can include a single wire strand wound into a close-packed coil that wraps around a lumen. The single wire strand therefore provides a coil wall surrounding the lumen. The first tether cable 510 and the second tether cable 514 can extend through a lumen (FIG. 10) of the retaining coil 902 such that the retaining coil constrains lateral movement of the first tether cable 510 relative to the second tether cable 514. When the tether cables 304 are so constrained, the central axes of the cables remain closely spaced rather than taking divergent paths that could result in connector misalignment and inadvertent release of the biostimulator 100.

Referring to FIG. 10, a cross-sectional view of a biostimulator delivery system is shown in accordance with an embodiment. The retaining coil 902 can have a distal end that is proximal to the distal cable ends 704 of the tethers 502, and can extend proximally through the docking cap 210 to a proximal end. More particularly, the retaining coil 902 can be longitudinally proximal to the distal cable ends 704 of the first and second tethers 510, 514.

In an embodiment, the tether assembly 214 includes one or more support tubes 1002 extending from the handle 202 to a tube end 1004. For example, the tether assembly 214 can include a first support tube 1002 terminating at a first tube end 1010, and a second support tube 1002 terminating at a second tube end 1012. The tether cables 304 can be coupled to the tube ends 1004 and extend from the tube ends 1004 to respective connectors 306. More particularly, the first tether cable 510 can be coupled to the first tube end 1010 and extend from the tube end to the first connector 508. Similarly, the second tether cable 514 can be coupled to the second tube end 1012 and extend from the tube end to the second connector 512. Accordingly, the tether cables 304 can extend distally from the support tubes 1002 through a lumen 1020 of the retaining coil 902 to respective connectors 306.

The connectors 306 and support tubes 1002 can be sized to retain the retaining coil 902 on the tether assembly 214. More particularly, the lumen 1020 of the retaining coil 902 can have a lumen diameter smaller than a combined cross-sectional dimension of the first support tube 1002 and the second support tube 1002. Similarly, the combined cross-sectional dimension of the first connector 508 and the second connector 512 may be greater than the lumen diameter. Accordingly, the retaining coil 902 may slide longitudinally along the tether cables 304, but may be blocked from sliding off of the tether assembly 214 both distally beyond the connectors 306, and proximally beyond the support tubes 1002.

In an embodiment, the support tubes 1002 are hypotubes. The hypotubes can have solid walls, which impart sufficient stiffness to the tether assembly 214 to allow longitudinal movement to be transmitted from the handle 202 to the tether cables 304. A proximal cable end 1022 of the tether cables 304 can be mechanically attached to the support tubes 1002. For example, the tether cables 304 can be inserted into an inner lumen of the hypotube, and the hypotube can be swaged or crimped onto the proximal cable end 1022.

The biostimulator delivery system 101 described above with respect to FIGS. 5-10 includes a non-limiting example of a tether assembly 214 having a cable tether 502. Other tether assemblies incorporating tether cables 304 may be contemplated, however. More particularly, a tether cable structure and/or connector structure may be changed while achieving the same benefits of tether flexibility and fatigue resistance.

Figure 11:
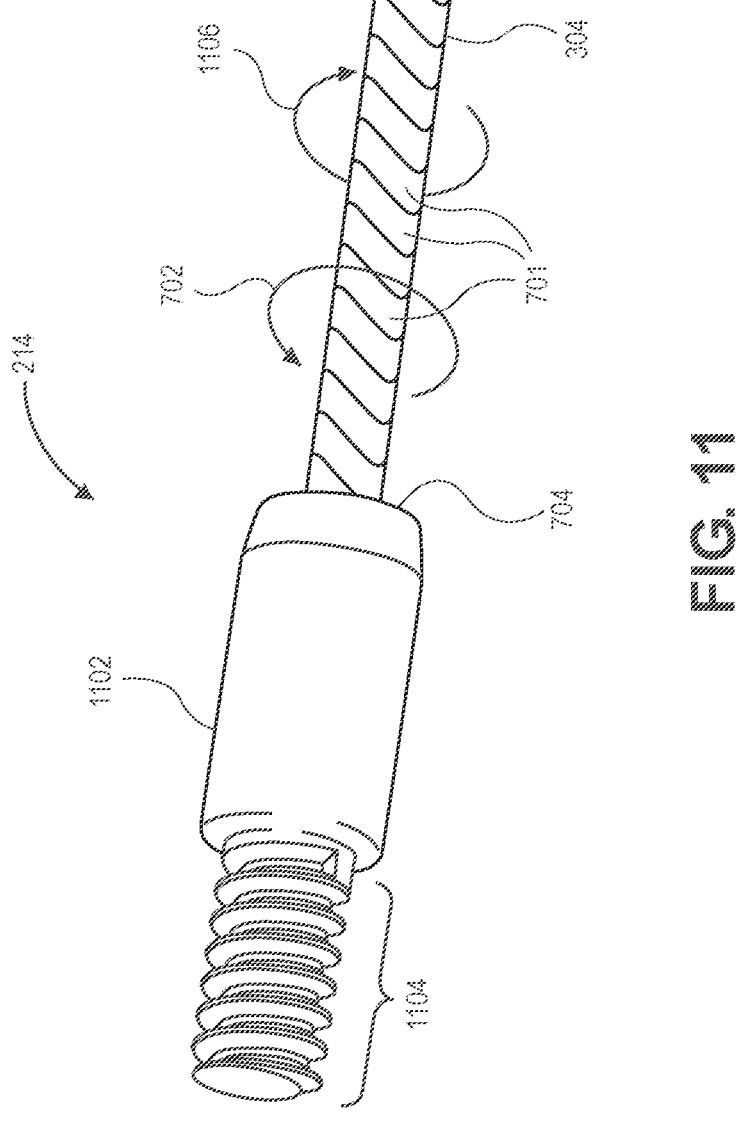
FIG. 11 is a perspective view of a tether assembly, in accordance with embodiment.

Referring to FIG. 11, a perspective view of a tether assembly is shown in accordance with embodiment. The tether assembly 214, which extends from the handle 202 through the elongated catheter 204, can include a threaded connector 1102 at the distal cable end 704 of the tether cable 304. More particularly, the connector 306 can include a threaded portion 1104 configured to screw into the attachment feature 102 of the biostimulator 100. The threaded portion 1104 can be machined into a connector body, and the connector body can be attached to the tether cable 304 via bonding processes such as welding, crimping, swaging, etc.

The tether cable 304 can include one or more strands 701 extending longitudinally along, or twisting about, the central axis of the tether. For example, one or more strands 701 may extend about the central axis in the first helical direction 702, and one or more strands 701 may extend about the central axis in a second helical direction 1106. The first helical direction 702 can be, e.g., clockwise about the central axis, and the second helical direction 1106 can be opposite to the first helical direction 702, e.g., counterclockwise about the central axis.

Figure 12:
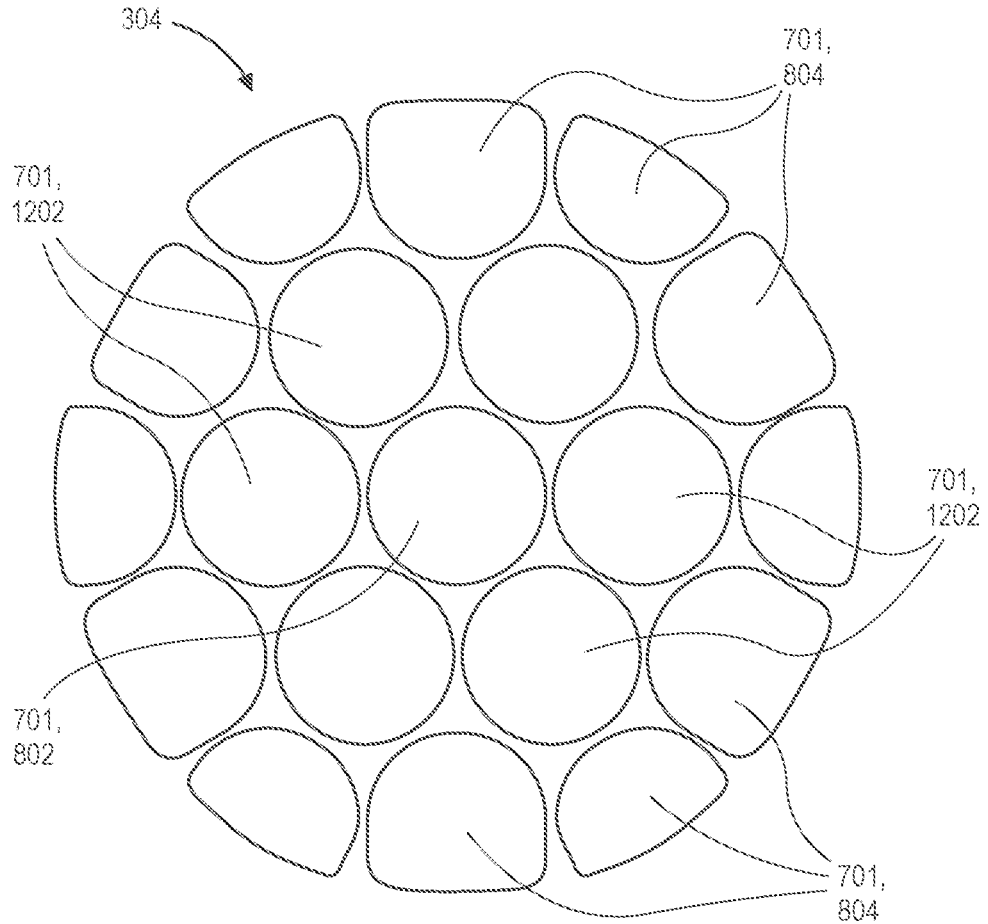
FIG. 12 is a cross-sectional view of a tether cable, in accordance with an embodiment.

Referring to FIG. 12, a cross-sectional view of a tether cable is shown in accordance with an embodiment. As described above, misalignment of the pair of connectors 306 in some embodiments can result in disengagement of the tether assembly 214 from the biostimulator 100. The threaded connector 1102, however, requires no alignment between connectors 306 and thus may reduce the likelihood of such an event. The tether assembly 214 incorporating the threaded connector 1102 may, however, be required to transmit torque. As such, an alternate tether cable 304 structure may be used.

In an embodiment, the tether cable 304 includes the core strand 802 and the first plurality of strands 804 described above. For example, the core strand 802 can extend longitudinally along the central axis, and the first plurality of strands 804 can wrap or twist about the core strand 802 in the first helical direction 702. To further contribute to torque transfer, the tether cable 304 may have a multi-layer structure that includes a second plurality of strands 1202 extending about the core strand 802 in the second helical direction 1106. The second plurality of strands 1202 can be radially between the core strand 802 and the first plurality of strands 804. For example, the second plurality of strands 1202 can be wrapped about the core strand 802, and the first plurality of strands 804 can then be wrapped about the second plurality of strands 1202. Accordingly, the second plurality of strands 1202 may be a first layer of strands and the first plurality of strands 804 may be a second layer of strands in a multi-layer structure.

The illustrated structure having the core strand 802 and two wrapped layers is provided by way of example, and more or fewer wrapped layers may be used. For example, in an embodiment, a four wrapped layer structure is used. The structure can be a 1×5×8×12×16 strand configuration, which refers to a single core strand 802, five strands in a first layer wrapped in a first direction about the core strand 802, eight strands in a second layer wrapped in a second direction about the first layer, twelve strands in a third layer wrapped in a third direction about the second layer, and sixteen strands in a fourth layer wrapped in a fourth direction about the third layer. The layers may be wrapped in opposite directions relative to the adjacent layers. For example, the five strands in the first layer and the twelve strands in the third layer may be wrapped clockwise, while the eight strands in the second layer can be wrapped counterclockwise.

The single, flexible, multi-filar stranded tether cable 304 can allow for torqueability in either a first direction, e.g., clockwise, or a second direction, e.g., counterclockwise. In an embodiment, the torqueability may be biased to be greater in a particular direction based on a wrapped direction of an outer layer of the cable. For example, when the outer layer of strands is wrapped about the core strand 802 in a clockwise direction (based on the right-hand rule) the tether cable 304 may have greater torqueability in the clockwise direction than in a counterclockwise direction. The bias can result from the outer layer of strands cinching down when the torque is applied, and thus creating a tighter composite of strands that is more efficiently twisted. Similarly, when the outer layer of strands is wrapped about the core strand 802 in a counterclockwise direction, the tether cable 304 may have greater torqueability in the counterclockwise direction.

As described above, the first plurality of strands 804 may be swaged to provide a cylindrical outer surface and to enhance the integrity of the cable structure. In the embodiment having four strand layers surrounding the core strand 802 (described above), each filar of the cable structure can have a same filar diameter, e.g., 0.0022 inch. The outer layer may then be swaged to reduce the combined dimension of the various strands to an 0.019 inch post-swaging diameter.

Referring to FIG. 13, a cross-sectional view of an attachment feature of the biostimulator is shown in accordance with an embodiment. The attachment feature 102 of the biostimulator 100 can have a channel 520 to receive the threaded connector 1102. Rather than having the step-shaped channel 520 of the attachment feature 102 that resists dislodgement, as described above, the channel 520 of the attachment feature 102 can have a channel thread 1302 to receive the threaded portion 1104 of the connector 306. The channel thread 1302 may include female threads that mate with male threads of the threaded portion 1104 of the connector 306 to attach the biostimulator 100 to the biostimulator delivery system 101.

Figure 14:
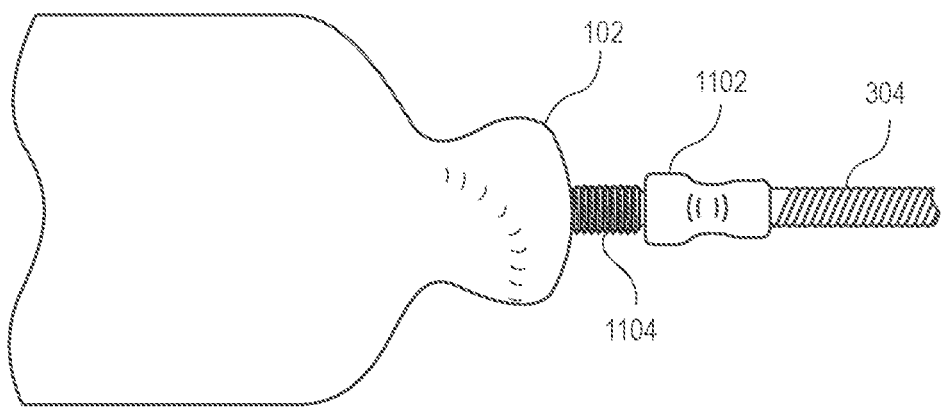
FIG. 14 is a side view of a threaded connector of the tether assembly engaging an attachment feature of a biostimulator, in accordance with an embodiment.

Referring to FIG. 14, a side view of a threaded connector of the tether assembly engaging an attachment feature of biostimulator is shown in accordance with an embodiment. Engagement and release of the biostimulator 100 may be enabled by rotating the tether cable 304 relative to the attachment feature 102. For example, when the threaded portion 1104 of the threaded connector 1102 has engaged the channel 520 of the attachment feature 102, the tether cable 304 can be twisted to screw the threaded portion 1104 into the channel thread 1302. Rotation of the tether cable 304 can be driven by the handle 202.

Figure 15:
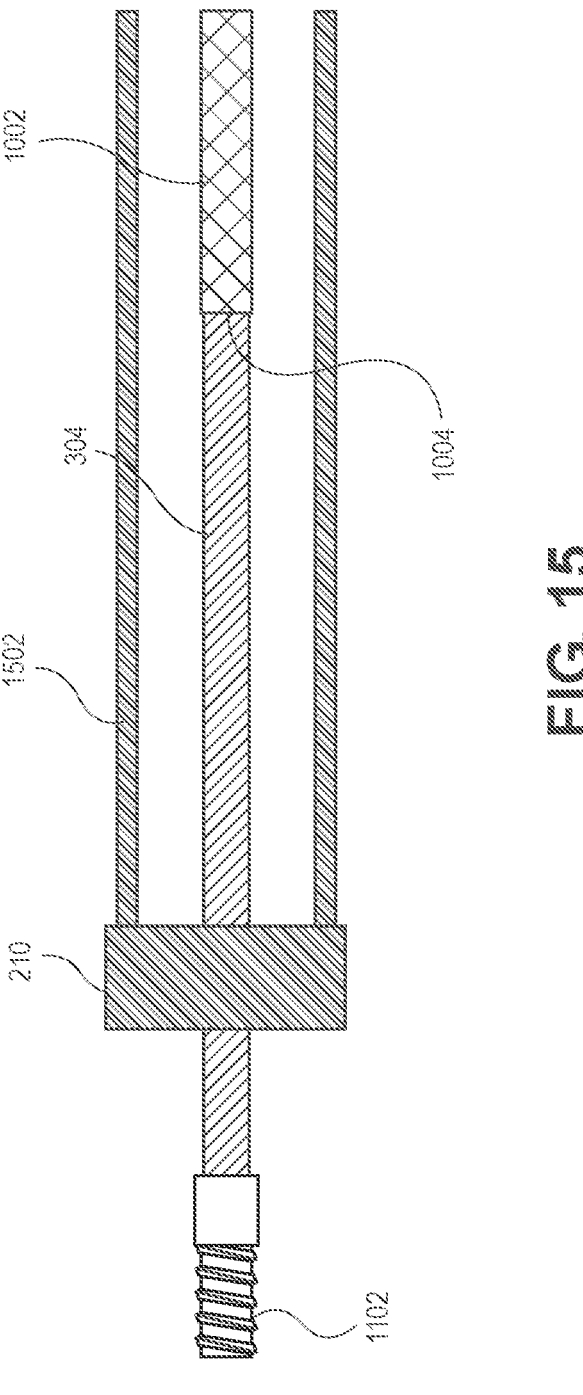
FIG. 15 is a cross-sectional view of a biostimulator delivery system, in accordance with an embodiment.

Referring to FIG. 15, a cross-sectional view of a biostimulator delivery system is shown in accordance with an embodiment. The biostimulator delivery system 101 can include a torque shaft 1502. The torque shaft 1502 can extend through the elongated catheter 204 from the handle 202 to the docking cap 210. As described above, the handle 202 can include the first handle portion 212 and the second handle portion 216. The first handle portion 212 can be coupled to torque shaft 1502 to transmit torque to the docking cap 210. Accordingly, when the attachment feature 102 is received within the docking cavity 308, rotation or counter rotation of the attachment feature 102 can be provided by the first handle portion 212. Similarly, the second handle portion 216 can be coupled to the tether cable 304 to transmit torque to the threaded connector 1102.

Like the tether assembly 214 described with respect to FIG. 10, the tether assembly 214 of FIG. 15 may include the support tube 1002 coupled to the tether cable 304. The support tube 1002 may extend from the handle 202 to the tube end 1004. More particularly, the support tube 1002 may be coupled to the second handle portion 216 at a proximal end of the support tube 1002. Furthermore, the tether cable 304 may be coupled to the tube end 1004 and extend from the tube end 1004 to the threaded connector 1102. Accordingly, rotation of the second handle portion 216 can transmit torque through the support tube 1002 and the tether cable 304 to the threaded connector 1102. When the threaded connector 1102 is engaged with the channel thread 1302, and the docking cap 210 is engaged with the attachment feature 102, relative rotation between the first handle portion 212 and the second handle portion 216 can therefore cause the threaded portion 1104 to either screw into or screw out of the attachment feature 102. Accordingly, like the two-tether embodiment described above, the single-tether embodiment can reliably support the biostimulator 100 in the tether mode, and can disengage from biostimulator 100 to implant the biostimulator 100 for pacing the target anatomy.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator delivery system, comprising:
a handle;
an elongated catheter extending from the handle;
a docking cap rotationally coupled to the elongated catheter, wherein the docking cap includes a docking cavity to receive an attachment feature of a biostimulator; and
a tether assembly extending from the handle through the elongated catheter, wherein the tether assembly includes a connector fixedly mounted on a tether cable such that the connector is immovable relative to the tether cable, wherein the tether cable extends longitudinally through a central hole in the connector to a distal cable end, wherein the distal cable end is exposed through the central hole of the connector, wherein the tether cable includes a core strand, a first plurality of strands extending about the core strand in a first helical direction between a proximal cable end and the distal cable end, and a second plurality of strands extending about the core strand in a second helical direction opposite the first helical direction and radially between the core strand and the first plurality of strands, wherein opposite helical directions comprise clockwise and counterclockwise, based on right-hand rule.

2. The biostimulator delivery system of claim 1, wherein the core strand has a round cross-sectional profile, and wherein the first plurality of strands have non- round cross-sectional profiles.

3. The biostimulator delivery system of claim 1, wherein the connector has an annular cross-sectional profile, and wherein a distal tip of the connector is dome-shaped.

4. The biostimulator delivery system of claim 1, wherein the tether assembly includes a support tube extending from the handle to a tube end, and wherein the tether cable is coupled to the tube end and extends from the tube end to the connector.

5. The biostimulator delivery system of claim 4, wherein the tether assembly includes a second connector at a second distal cable end of a second tether cable, wherein the tether assembly includes a second support tube extending from the handle to a second tube end, and wherein the second tether cable is coupled to the second tube end and extends from second tube end to the second connector.

6. The biostimulator delivery system of claim 1, wherein the tether assembly includes a second connector at a second distal cable end of a second tether cable, and a retaining coil, and wherein the tether cable and the second tether cable extend through a lumen of the retaining coil such that the retaining coil constrains lateral movement of the tether cable relative to the second tether cable.

7. The biostimulator delivery system of claim 1, wherein the connector includes a threaded portion configured to screw into the attachment feature.

8. The biostimulator delivery system of claim 7 further comprising a torque shaft extending through the elongated catheter from the handle to the docking cap, wherein the handle includes a first handle portion coupled to the torque shaft to transmit torque to the docking cap, and wherein the handle includes a second handle portion coupled to the tether cable to transmit torque to the connector.

9. A biostimulator delivery system, comprising:
a handle;
an elongated catheter extending from the handle;
a docking cap rotationally coupled to the elongated catheter, wherein the docking cap includes a docking cavity to receive an attachment feature of a biostimulator; and
a tether assembly extending from the handle through the elongated catheter, wherein the tether assembly includes
a first connector mounted on a first tether cable, and a second connector mounted on a second tether cable, wherein the first tether cable extends longitudinally through a central hole in the first connector to a distal cable end, and wherein the distal cable end is exposed through the central hole of the first connector, the first connector fixedly mounted on the first tether cable at the distal cable end such that the first connector is immovable relative to the first tether cable, wherein the first tether cable includes a core strand, a first plurality of strands extending about the core strand in a first helical direction between a proximal cable end and the distal cable end, and a second plurality of strands extending about the core strand in a second helical direction opposite the first helical direction and radially between the core strand and the first plurality of strands, wherein opposite helical directions comprise clockwise and counterclockwise, based on right-hand rule.

10. The biostimulator delivery system of claim 9, wherein the tether assembly includes a first support tube extending from the handle to a first tube end, and a second support tube extending from the handle to a second tube end, wherein the first tether cable is coupled to the first tube end and extends from the first tube end to the first connector, and wherein the second tether cable is coupled to the second tube end and extends from the second tube end to the second connector.

11. The biostimulator delivery system of claim 10, wherein the tether assembly includes a retaining coil, and wherein the first tether cable and the second tether cable extend through a lumen of the retaining coil such that the retaining coil constrains lateral movement of the first tether cable relative to the second tether cable.

12. The biostimulator delivery system of claim 11, wherein the lumen of the retaining coil has a lumen diameter smaller than a combined cross-sectional dimension of the first support tube and the second support tube.

13. A biostimulator delivery system, comprising:
a handle;
an elongated catheter extending from the handle;
a docking cap rotationally coupled to the elongated catheter, wherein the docking cap includes a docking cavity to receive an attachment feature of a biostimulator; and
a tether assembly extending from the handle through the elongated catheter, wherein the tether assembly includes a threaded connector fixedly mounted on a distal cable end of a tether cable, and wherein the tether cable extends longitudinally through a central hole in the threaded connector, wherein the tether cable includes a core strand, a first plurality of strands extending about the core strand in a first helical direction between a proximal cable end and the distal cable end, and a second plurality of strands extending about the core strand in a second helical direction opposite the first helical direction and radially between the core strand and the first plurality of strands, wherein opposite helical directions comprise clockwise and counterclockwise, based on right-hand rule.

14. The biostimulator delivery system of claim 13, wherein the tether assembly includes a support tube extending from the handle to a tube end, and wherein the tether cable is coupled to the tube end and extends from the tube end to the threaded connector.

15. The biostimulator delivery system of claim 13, wherein the threaded connector includes a threaded portion configured to screw into the attachment feature.

16. The biostimulator delivery system of claim 13, further comprising a torque shaft extending through the elongated catheter from the handle to the docking cap, wherein the handle includes a first handle portion coupled to the torque shaft to transmit torque to the docking cap, and wherein the handle includes a second handle portion coupled to the tether cable to transmit torque to the threaded connector.

* * * * *